US 11,245,884 B2

(12) United States Patent
Yamaguchi et al.

(10) Patent No.: US 11,245,884 B2
(45) Date of Patent: Feb. 8, 2022

(54) CONTROL APPARATUS, CONTROL SYSTEM, AND CONTROL METHOD FOR TRANSMISSION OF A BIOLOGICAL IMAGE

(71) Applicant: SONY CORPORATION, Tokyo (JP)

(72) Inventors: Kenta Yamaguchi, Kanagawa (JP); Daisuke Kikuchi, Kanagawa (JP); Hisakazu Shiraki, Kanagawa (JP); Masahito Yamane, Kanagawa (JP); Kenji Ikeda, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/474,246

(22) PCT Filed: Nov. 15, 2017

(86) PCT No.: PCT/JP2017/041097
§ 371 (c)(1),
(2) Date: Jun. 27, 2019

(87) PCT Pub. No.: WO2018/128010
PCT Pub. Date: Jul. 12, 2018

(65) Prior Publication Data
US 2019/0356890 A1 Nov. 21, 2019

(30) Foreign Application Priority Data
Jan. 6, 2017 (JP) .............................. JP2017-000879

(51) Int. Cl.
H04N 9/64 (2006.01)
A61B 1/045 (2006.01)
(Continued)

(52) U.S. Cl.
CPC .............. H04N 9/64 (2013.01); A61B 1/045 (2013.01); A61B 1/0638 (2013.01);
(Continued)

(58) Field of Classification Search
CPC ...... H04N 9/64; H04N 5/2351; H04N 5/2354; H04N 2005/2255; H04N 5/2256;
(Continued)

(56) References Cited

U.S. PATENT DOCUMENTS 5,331,551 A * 7/1994 Tsuruoka ................. A61B 1/05
348/71
5,703,622 A * 12/1997 Evans ...................... G09G 5/06
345/603

(Continued)

FOREIGN PATENT DOCUMENTS

JP 02-266476 A 10/1990
JP 2015-037565 A 2/2015
(Continued)

OTHER PUBLICATIONS

International Search Report and Written Opinion of PCT Application No. PCT/JP2017/041097, dated Dec. 19, 2017, 10 pages of ISRWO.

Primary Examiner — Albert H Cutler
(74) Attorney, Agent, or Firm — Chip Law Group

(57) ABSTRACT

Provided is a control apparatus including a ratio calculation unit that calculates a first ratio of a bit assignment relating to transmission of a biological image on the basis of image capture conditions and a bit assignment determination unit that determines the bit assignment on the basis of the first ratio. In addition, provided is a control system including an image capture apparatus that captures an image of an object, the control apparatus including the ratio calculation unit that calculates the first ratio on the basis of the image capture conditions relating to the object, the bit assignment determination unit that determines the bit assignment, an image processing unit that performs image processing based on the captured image and the bit assignment and generates the (Continued)

biological image, and an output apparatus that outputs the biological image based on the bit assignment.

16 Claims, 14 Drawing Sheets

(51) Int. Cl.
    *A61B 1/06*         (2006.01)
    *H04N 5/235*      (2006.01)
    *H04N 5/225*      (2006.01)
    *A61B 1/04*         (2006.01)
    *A61B 1/00*         (2006.01)
    *H04N 5/232*      (2006.01)
    *G02B 23/24*      (2006.01)

(52) U.S. Cl.
    CPC ......... *H04N 5/2351* (2013.01); *H04N 5/2354* (2013.01); *H04N 2005/2255* (2013.01)

(58) Field of Classification Search
    CPC .. H04N 9/0451; H04N 5/23203; A61B 1/045; A61B 1/0638; A61B 1/043; A61B 1/0009; A61B 1/00; G02B 23/24
    USPC .................................................. 348/370, 371
    See application file for complete search history.

(56) References Cited

U.S. PATENT DOCUMENTS

| | | | |
|---|---|---|---|
| 7,158,178 B1* | 1/2007 | Acharya | H04N 9/045 348/234 |
| 2002/0025083 A1* | 2/2002 | Asano | H04N 5/44504 382/298 |
| 2005/0099424 A1* | 5/2005 | Skaletzky | H04N 9/64 345/506 |
| 2005/0259729 A1* | 11/2005 | Sun | H04N 19/33 375/240.1 |
| 2017/0011690 A1* | 1/2017 | Oya | G09G 3/3426 |
| 2017/0020378 A1* | 1/2017 | Godo | A61B 1/0638 |
| 2018/0278965 A1* | 9/2018 | Dsouza | H04N 19/85 |
| 2019/0058841 A1* | 2/2019 | Yamashita | A61B 1/045 |
| 2019/0110669 A1* | 4/2019 | Furuho | A61B 1/045 |

FOREIGN PATENT DOCUMENTS

| | | |
|---|---|---|
| JP | 2016-152920 A | 8/2016 |
| WO | 2013/069691 A1 | 5/2013 |

* cited by examiner

CONTROL APPARATUS, CONTROL SYSTEM, AND CONTROL METHOD FOR TRANSMISSION OF A BIOLOGICAL IMAGE

CROSS REFERENCE TO RELATED APPLICATIONS

This application is a U.S. National Phase of International Patent Application No. PCT/JP2017/041097 filed on Nov. 15, 2017, which claims priority benefit of Japanese Patent Application No. JP 2017-000879 filed in the Japan Patent Office on Jan. 6, 2017. Each of the above-referenced applications is hereby incorporated herein by reference in its entirety.

TECHNICAL FIELD

The present disclosure relates to a control apparatus, a control system, and a control method.

BACKGROUND ART

In recent years, a variety of apparatuses that apply image processing to a captured biological image are widely used. In addition, many techniques relating to a transmission of the processed biological image are proposed. For example, Patent Literature 1 discloses a technique of limiting a transmission amount upon transmission of the biological image on the basis of a communication state with an output apparatus.

CITATION LIST

Patent Literature

Patent Literature 1: PCT International Application Publication No. 2013/069691

DISCLOSURE OF INVENTION

Technical Problem

However, the technique described in Patent Literature 1 is a technique that the communication state can be improved or maintained by lowering the transmission amount. Therefore, by the technique of Patent Literature 1, it is difficult to keep an image quality of the biological image high. In addition, the biological image is captured under a variety of image capture conditions. It is difficult to say that a general transmission standard of the biological image is suitable to the above-described image capture conditions and characteristics of an output apparatus.

Accordingly, the present disclosure proposes a novel and improved control apparatus, a novel and improved control system, and a novel and improved control method that allow the transmission of the biological image suitable to the image capture conditions and characteristics of an output apparatus.

Solution to Problem

The present disclosure discloses a control apparatus including a ratio calculation unit calculating a first ratio of a bit assignment relating to transmission of a biological image on the basis of image capture conditions and a bit assignment determination unit determining the bit assignment on the basis of the first ratio.

In addition, the present disclosure provides a control system including an image capture apparatus including an image capture unit capturing an object, a control apparatus including a ratio calculation unit calculating a first ratio of a bit assignment relating to transmission of a biological image on the basis of image capture conditions relating to the object, a bit assignment determination unit determining the bit assignment on the basis of the first ratio, and an image processing unit performing image processing based on an image captured by the image capture unit and the bit assignment and generating the biological image, and an output apparatus including an output unit performing an output relating to the biological image based on the bit assignment.

In addition, the present disclosure provides a control method including calculating a first ratio of a bit assignment relating to transmission of a biological image on the basis of image capture conditions by a processor, and determining the bit assignment on the basis of the first ratio by the processor.

Advantageous Effects of Invention

As described above, according to the present disclosure, it becomes possible to realize the transmission of the biological image suitable to the image capture conditions and characteristics of an output apparatus.

It should be noted that the effects described here are not necessarily limitative and may be any of effects described in the present disclosure or other effects conceivable from the present specification together with the above-described effects and in addition to the above-described effects.

MODE(S) FOR CARRYING OUT THE INVENTION

Figure 1:
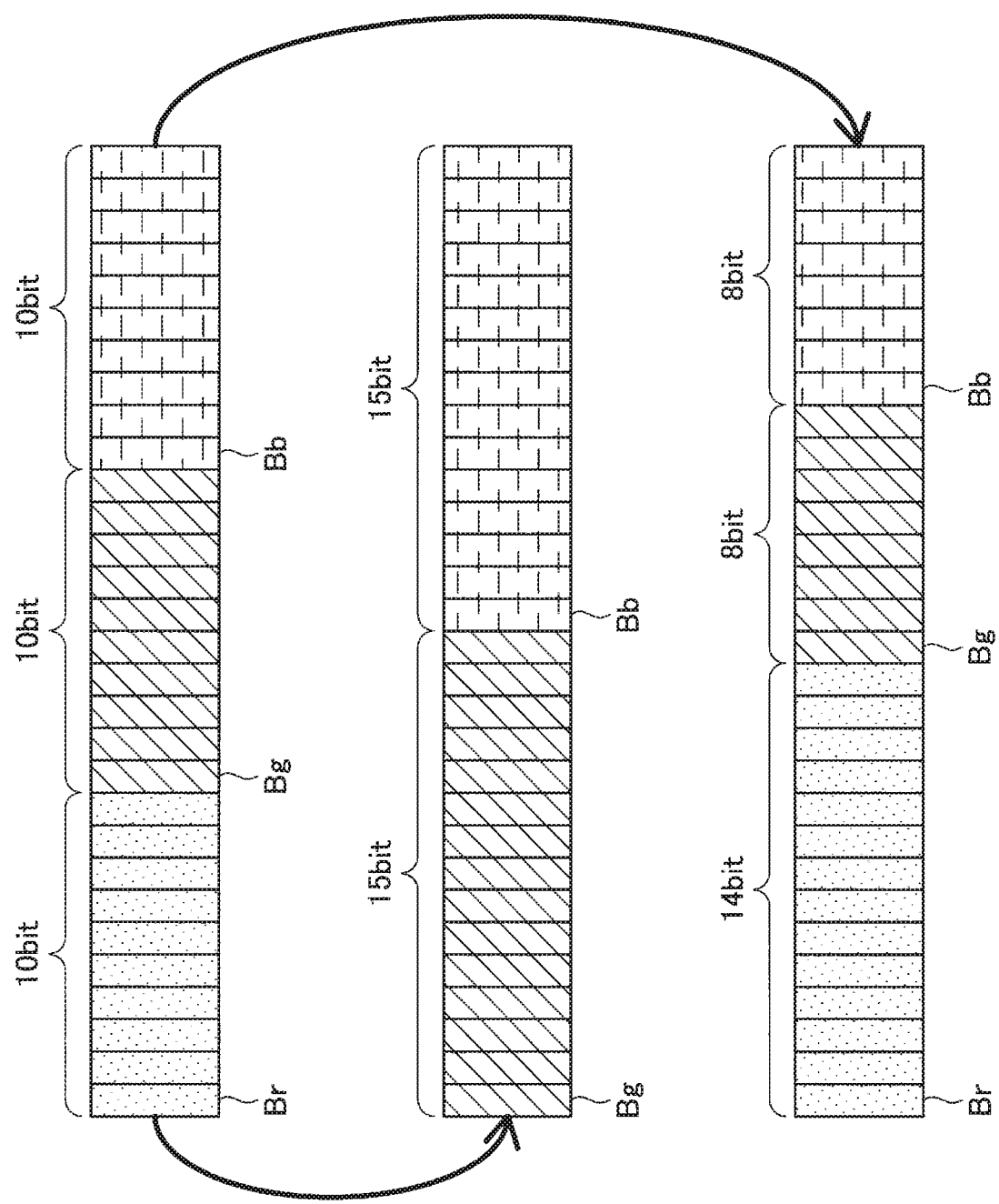
FIG. 1 is a diagram for describing a bit assignment conversion by a control apparatus according to an embodiment of the present disclosure.

Hereinafter, an embodiment of the present disclosure will be described with reference to the drawings.

Hereinafter, preferable embodiments according to the present disclosure will be described in detail with reference to the drawings. Note that, components having the substantially same functional configurations are denoted by the same reference numerals in the present specification and drawings, and thus overlapping description thereof will be omitted.

The description will be made in the following order.
1. Embodiment
  1.1. Overview of embodiment
  1.2. Configuration example of control system 1000
  1.3. Functional configuration example of light source apparatus 10
  1.4. Functional configuration example of image capture apparatus 20
  1.5. Functional configuration example of control apparatus
  1.6. Output apparatus 40
  1.7. Details of bit assignment
  1.8. Operation flow of control apparatus 30
2. Hardware configuration example
3. Summary <1. Embodiment>
<<1.1. Overview of Embodiment>>

In recent years, capturing a biological image is widely performed in a variety of operative procedures, pathological diagnoses, scientific validation experiments, and the like. In addition, a variety of systems that capture and output the above-described biological image are proposed. For example, in a general endoscope system, a RAW signal captured by an image capture apparatus is subject to develop processing, high image quality processing, and the like by a signal processing apparatus (Camera Control Unit: CCU) and is transmitted to an output apparatus.

On the other hand, the biological image is captured under a variety of image capture conditions including White Light Imaging (WLI) using white light. Examples of the above-described image capture conditions include, for example, special light imaging such as Narrow Band Imaging (NBI), Auto Fluorescence Imaging (AFI), and Infra-Red Imaging (IRI).

However, for example, in a 3G-SGI that is a general transmission standard of 4K resolution, a 3ch signal by RGB or YCC is transmitted in 10 bits or 12 bits. Accordingly, the same transmission standard is used in the white light imaging as well as the special light imaging that does not use specific color information, which results in unnecessary signals generated in a part of the transmitted signals. Specifically, in a case where the output apparatus outputs the biological image captured by the special light imaging, an amount of usable information is less as compared with the white light imaging in which all transmitted signals are usable, and it is thus difficult to realize sufficient image quality with respect to transmitted signal information.

In addition, also in a transmission of a biological image captured by the white light imaging, it assumes a transmission of normal use image, for example, in a widely used standard such as ITU-R BT.709 and ITU-R BT.2020. Therefore, if the output apparatus that outputs the biological image has a color gamut wider than the standard, it is difficult to sufficiently utilize a performance.

The control apparatus, the control system, and the control method according to the present embodiment are devised by focusing on the above-described points and can realize the transmission of the biological image corresponding to the image capture conditions and characteristics of the output apparatus. Therefore, the control apparatus, the control system, and the control method according to the present embodiment are characterized in that the bit assignment relating to the transmission of the biological image is determined on the basis of the image capture conditions and the output characteristics.

FIG. 1 is a diagram for describing a bit assignment conversion by a control apparatus 30 according to the present embodiment. On the upper row of FIG. 1, an example of a bit assignment of a biological image transmitted from an image capture apparatus 20. Here, a bit Br, a bit Bg, a bit Bb show bits corresponding to signals of red (R), green (G), and blue (B), respectively. In other words, the biological image captured by the image capture apparatus 20 is transmitted to the control apparatus 30 in the state of 10 bits for each 3ch of RGB.

In this case, the control apparatus 30 according to the present embodiment can convert the bit assignment on the basis of the image capture conditions of the biological image and transfer the biological image to an output apparatus 40.

For example, since an image is captured by wavelengths of green and blue light in narrow band imaging, the output apparatus 40 does not need color information about red. Therefore, in a case where the biological image is captured by the narrow band imaging, the control apparatus 30 may perform the bit assignment conversion in which bits to be originally assigned to R are allocated to G and B. On the middle row of FIG. 1, an example of a bit assignment conversion performed by the control apparatus 30 in a case where the biological image is captured by narrow band imaging. As shown in FIG. 1, the control apparatus 30 may determine the bit assignment such that the bit Bg corresponding to G and the bit Bb corresponding to B are 15 bits, respectively. According to the above-described functions included in the control apparatus 30, the output apparatus 40 can output a high quality biological image suitable to the image capture conditions.

In addition, the control apparatus 30 according to the present embodiment can also convert the bit assignment and transfer the biological image to the output apparatus 40 on the basis of the output characteristics of the output apparatus 40.

For example, in a case where the output apparatus 40 has a color gamut in R wider than the standard, the control apparatus 30 may set a greater number of bits assigned to R than those assigned to G or B. On the lower row of FIG. 1, an example of a bit assignment performed by the control apparatus 30 in a case where the output apparatus 40 has a wide color gamut in R. As shown in FIG. 1, the control apparatus 30 may determine the bit assignment such that the bit Br, the bit Bg, and the bit Bb are, for example, 14 bits, 8 bits, 8 bits, respectively. According to the above described functions included in the control apparatus 30, it becomes possible to provide a high quality biological image depending on the characteristics of the output apparatus 40.

An overview of the bit assignment conversion by the control apparatus 30 according to the present embodiment is described above. The control apparatus 30 according to the present embodiment can determine the bit assignment depending on the image capture conditions of the biological image and the output characteristics of the output apparatus 40, as described above. According to the above-described features included in the control apparatus 30 according to the present embodiment, it becomes possible to provide a high quality biological image suitable for the image capture conditions and the output characteristics.

<<1.2. Configuration Example of Control System 1000>>

Figure 2:
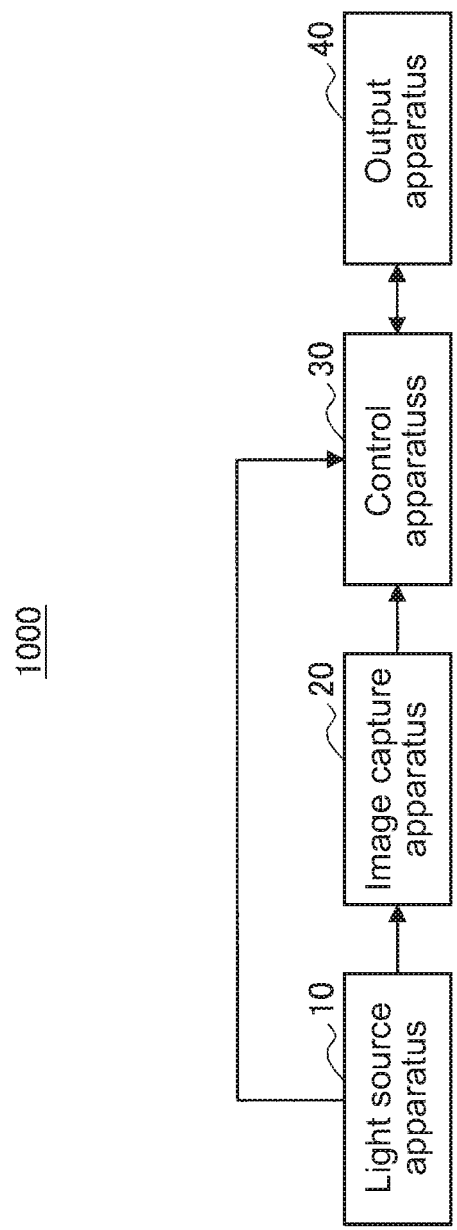
FIG. 2 is a diagram showing a basic configuration of the control system according to the embodiment.

Next, a basic configuration of a control system 1000 according to the present embodiment will be described. FIG. 2 is a diagram showing a basic configuration of the control system 1000 according to the embodiment. With reference to FIG. 2, the control system 1000 according to the present embodiment includes a light source apparatus 10, an image capture apparatus 20, a control apparatus 30, and an output apparatus 40. In addition, each apparatus described above is connected via wire or wireless networks so as to perform mutual information communication.

(Light Source Apparatus 10)

The light source apparatus 10 according to the present embodiment includes a variety of light sources such as an LED (light emitting diode). In addition, the light source apparatus 10 according to the present embodiment has a function to feed irradiation light when an object such as an operative part is captured by the image capture apparatus 20. Note that the light source apparatus 10 according to the present embodiment has a function to send information about an image capture mode to the image capture apparatus 20 and the control apparatus 30. Here, the above-described image capture mode includes a white light imaging mode, a narrow band imaging mode, an auto fluorescence imaging mode, an infra-red imaging mode, and the like.

(Image Capture Apparatus 20)

The image capture apparatus 20 according to the present embodiment includes an image sensor for capturing the biological image. The image capture apparatus 20 according to the present embodiment sends the RAW signal relating to the captured biological image to the control apparatus 30 via a camera cable or a wireless communication. Here, the biological image according to the present embodiment includes a wide variety of images acquired from a biological perspective view (Biological Imaging) for clinical, medical, and experimental applications, and the object to be captured is not limited to human. In addition, the image capture apparatus 20 according to the present embodiment may send the information about the above-described image capture mode to the control apparatus 30.

(Control Apparatus 30)

The control apparatus 30 according to the present embodiment is a signal processing apparatus that performs a variety of processing with respect to the biological image captured by the image capture apparatus 20. The control apparatus 30 performs, for example, develop processing and high image quality processing with respect to the transmitted RAW signal.

In addition, the control apparatus 30 according to the present embodiment has a function to determine the bit assignment relating to the transmission of the biological image on the basis of the image capture conditions of the biological image and the output characteristics of the output apparatus 40. The above-described function included in the control apparatus 30 of according to the present embodiment will be separately described in detail. In addition, the control apparatus 30 transmits the biological image to the output apparatus 40 on the basis of the determined bit assignment. In this case, the control apparatus 30 according to the present embodiment may send the information about the determined bit assignment to the output apparatus 40 together with the biological image.

(Output Apparatus 40)

The output apparatus 40 according to the present embodiment can be realized by a variety of apparatuses including a function to output the transmitted biological image. The output apparatus 40 according to the present embodiment may be a variety of display apparatuses, printing apparatuses, and the like, for example. The output apparatus 40 according to the present embodiment can output the biological image transmitted from the control apparatus 30 on the basis of the information about the bit assignment transmitted together with the biological image. In addition, the output apparatus 40 may send output characteristics such as a color gamut and a gamma curve to the control apparatus 30.

The basic configuration of the control system according to the present embodiment is described above. Note that the above-described basic configuration described by using FIG. 2 is just illustrative and the basic configuration of the control system according to the present embodiment is not limited thereto. The control system according to the present embodiment may include configurations other than those shown in the above and the above-shown functions included in the apparatuses may be realized by distributing to a plurality of apparatuses.

Figure 3:
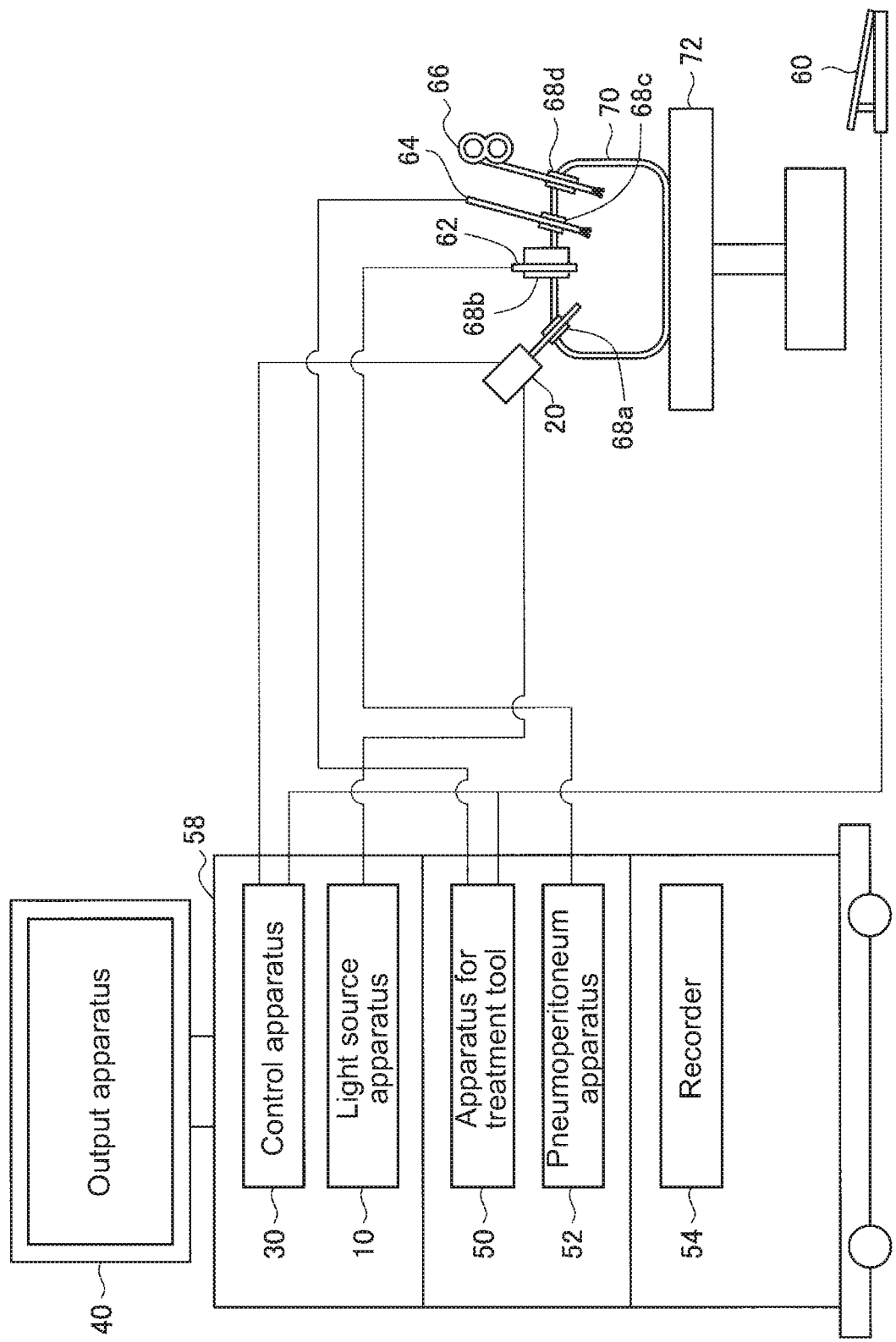
FIG. 3 is a diagram showing a configuration example in a case where the control system according to the embodiment is realized as an endoscope system.

Subsequently, a configuration example of the control system 1000 according to the present embodiment will be described in a case where the system 1000 is realized as an endoscope system. FIG. 3 is a diagram showing the configuration example in a case where the control system 1000 according to the embodiment is realized as the endoscope system. FIG. 3 shows a state that a surgeon (not shown) performs surgery on a patient 70 above a patient bed 72 by using the control system. As shown in FIG. 3, the control system 1000 according to the present embodiment includes the image capture apparatus 20, other operation tools, and a cart 58 on which a variety of apparatuses used for the operation are mounted.

In the endoscope surgery, an abdominal wall is punctured by a plurality of tube-shaped opening devices called as trocars 68a to 68d instead of cutting the abdominal wall and opening an abdomen. Then, from the trocars 68a to 68d, the image capture apparatus 20, e.g., an endoscope (laparoscopic) and other operation tools are inserted into a body cavity of the patient 70. In the shown example, a pneumoperitoneum tube 62, an energy treatment tool 64, and forceps 66 are inserted into the body cavity of the patient 70 as other operation tools.

Note that the energy treatment tool 64 is a treatment tool for incising and peeling a tissue, sealing a blood vessel, or the like by using a high-frequency current or an ultrasonic vibration. In addition, the apparatus for treatment tool 50 according to the present embodiment controls driving of the energy treatment tool 64 for cauterizing or cutting the tissue, sealing the blood vessel, or the like. Therefore, the apparatus for treatment tool 50 according to the present embodiment may be a high-frequency output apparatus that outputs a high-frequency current to the energy treatment tool 64.

In addition, a pneumoperitoneum apparatus 52 according to the present embodiment is an apparatus that feeds gas into the body cavity via the pneumoperitoneum tube 62 and inflates the body cavity of the patient 70 in order to ensure an angle of view of the image capture apparatus 20 and ensure a work space of the surgeon. However, the shown operation tool is just illustrative and a variety of operation tools generally used in the endoscopic surgery such as tweezers and retractor may be used as other operation tools.

In addition, the biological image of the body cavity of the patient 70 captured by the image capture apparatus 20 is outputted from the output apparatus 40. While the surgeon can check the biological image outputted from the output apparatus 40 in real time, the surgeon can perform treatment such as cutting, for example, a diseased part by using the energy treatment tool 64, and the forceps 66. Note that although not shown, the image capture apparatus 20, the pneumoperitoneum tube 62, the energy treatment tool 64, and the forceps 66 may be supported by the surgeon, an assistant, a scopist, a variety of robots, or the like during the surgery. In addition, the control apparatus 30, the apparatus for treatment tool 50, and the like may be controlled on the basis of an operation of a foot switch 60 by the surgeon, the assistant, or the like.

In addition, a recorder 54 according to the present embodiment is an apparatus capable of recording a variety of information about the surgery. The recorder 54 can record, for example, a vital sign, and the like of the patient 70.

The control system 1000 according to the present embodiment is described above by taking the endoscope system as an embodied example. Note that the above-described configuration described by using FIG. 3 is just illustrative and the configuration of the control system according to the present embodiment is not limited to the example. In addition, the control system according to the present embodiment is not limited to the endoscope system. The control system according to the present embodiment may be applicable to a variety of systems that capture and output the biological image.

<<1.3. Functional Configuration Example of Light Source Apparatus 10>>

Figure 4:
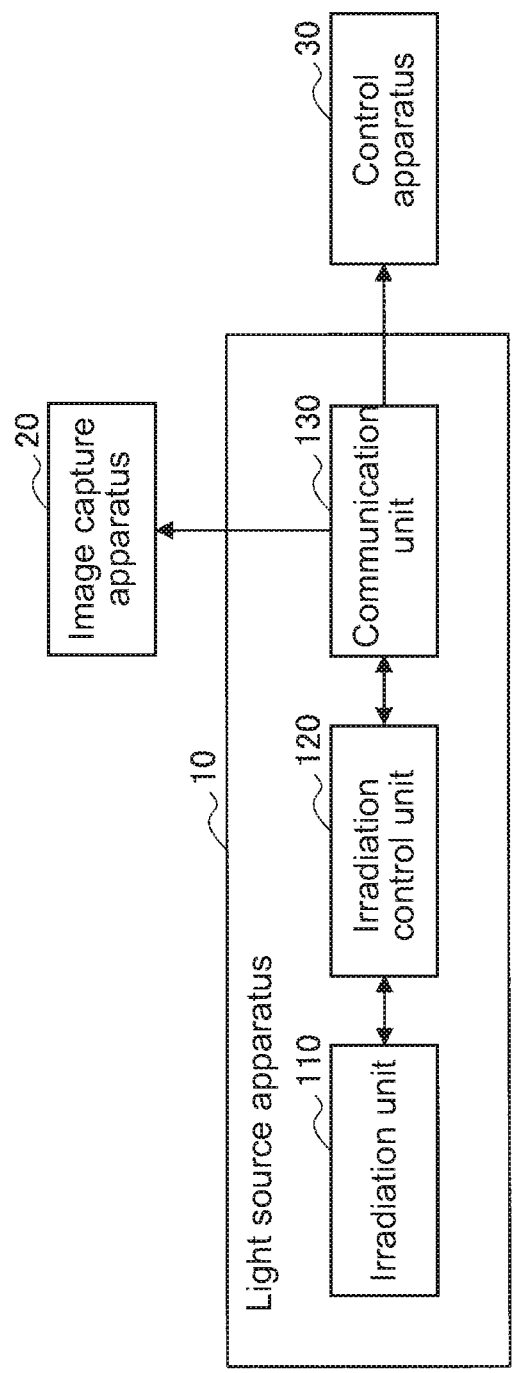
FIG. 4 is a functional block diagram of a light source apparatus according to the embodiment.

Next, a functional configuration example of the light source apparatus 10 according to the present embodiment will be described. FIG. 4 is a functional block diagram of the light source apparatus 10 according to the embodiment. With reference to FIG. 4, the light source apparatus 10 according to the present embodiment includes an irradiation unit 110, an irradiation control unit 120, and a communication unit 130.

(Irradiation Unit 110)

The irradiation unit 110 has a function to irradiate the object to be captured by the image capture apparatus 20 with light. The irradiation unit 110 according to the present embodiment may irradiate the object with light by using a light source depending on the image capture mode on the basis of the control by the irradiation control unit 120.

(Irradiation Control Unit 120)

The irradiation control unit 120 has a function to cause the irradiation unit 110 to irradiate light depending on the image capture mode on the basis of an input operation by a user such as the surgeon. The irradiation control unit 120 may cause the irradiation unit 110 to irradiate light of green and blue wavelengths in, for example, the narrow band imaging.

(Communication Unit 130)

The communication unit 130 has a function to send the information about the image capture mode to the image capture apparatus 20 and the control apparatus 30. In this case, the communication unit 130 may send the information about the above-described image capture mode to both of the image capture apparatus 20 and the control apparatus 30 or may send to any one of them. A send destination of the information about the image capture mode may be designed depending on the specification, the operation, and the like of the control system 1000, as appropriate. In addition, the communication unit 130 can dynamically send the information about the image capture mode on the basis that the communication between the image capture apparatus 20 and the control apparatus 30 is ensured, for example.

The functional configuration example of the light source apparatus 10 according to the present embodiment is described above. Note that the above-described configuration described by using FIG. 4 is just illustrative and the functional configuration of the light source apparatus 10 according to the present embodiment is not limited thereto. The light source apparatus 10 may further include an input unit that accepts the user's input operation, for example. The functional configuration of the light source apparatus 10 according to the present embodiment can be flexibly deformed.

<<1.4. Functional Configuration Example of Image Capture Apparatus 20>>

Figure 5:
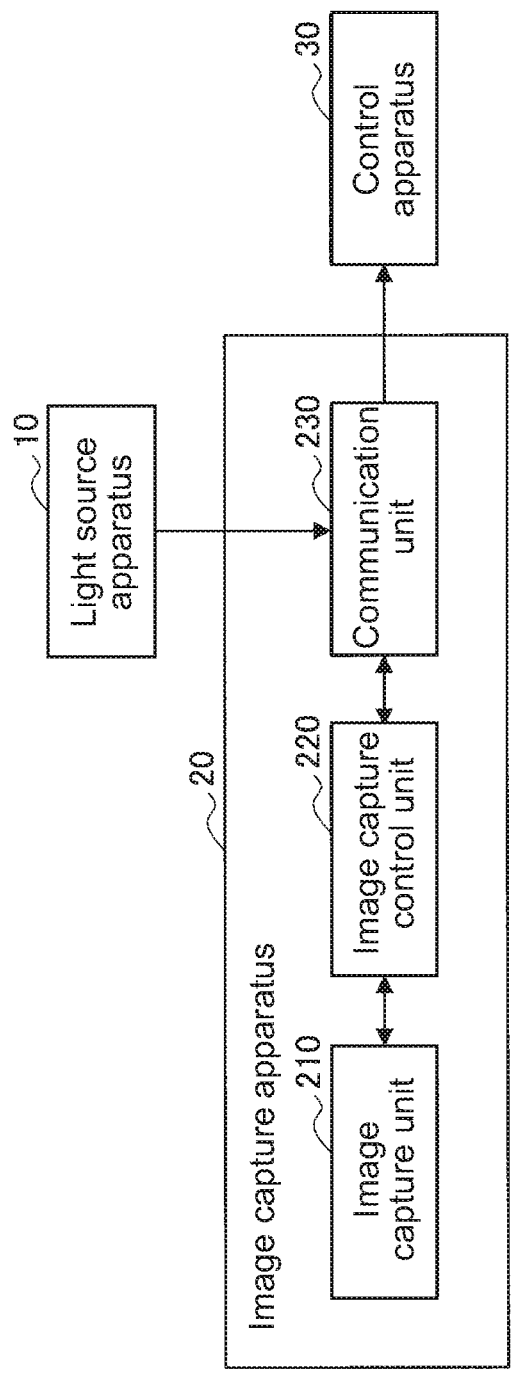
FIG. 5 is a functional block diagram of an image capture apparatus according to the embodiment.

Next, a functional configuration example of the image capture apparatus 20 according to the present embodiment will be described. FIG. 5 is a functional block diagram of the image capture apparatus 20 according to the embodiment. With reference to FIG. 5, the image capture apparatus 20 according to the present embodiment includes an image capture unit 210, an image capture control unit 220, and a communication unit 230.

(Image Capture Unit 210)

The image capture unit 210 has a function to capture the biological image of the object. Therefore, the image capture unit 210 according to the present embodiment includes the image sensor such as a CCD (Charge Coupled Device) and a CMOS (Complementary MOS).

(Image Capture Control Unit 220)

The image capture control unit 220 has a function to control the image capture of the biological image by the image capture unit 210. The image capture control unit 220 may control the image capture unit 210 on the basis of the input operation by the user such as the surgeon, for example.

(Communication Unit 230)

The communication unit 230 has a function to transmit the RAW signal relating to the object acquired by the image capture unit 210 to the control apparatus 30. In addition, the communication unit 230 according to the present embodiment may send the information about the image capture mode received from the light source apparatus 10 to the control apparatus 30 together with the RAW signal. In this case, the communication unit 230 can dynamically send the information about the image capture mode on the basis that the communication between the communication unit 230 and the control apparatus 30 is established.

The functional configuration example of the image capture apparatus 20 according to the present embodiment is described above. Note that the above-described configuration described by using FIG. 5 is just illustrative and the functional configuration of the image capture apparatus 20 according to the present embodiment is not limited thereto. The image capture apparatus 20 may further include the input unit that accepts the user's input operation, for example. The functional configuration of the input unit according to the present embodiment can be flexibly deformed.

<<1.5. Functional Configuration Example of Control Apparatus 30>>

(Control Apparatus 30)

Figure 6:
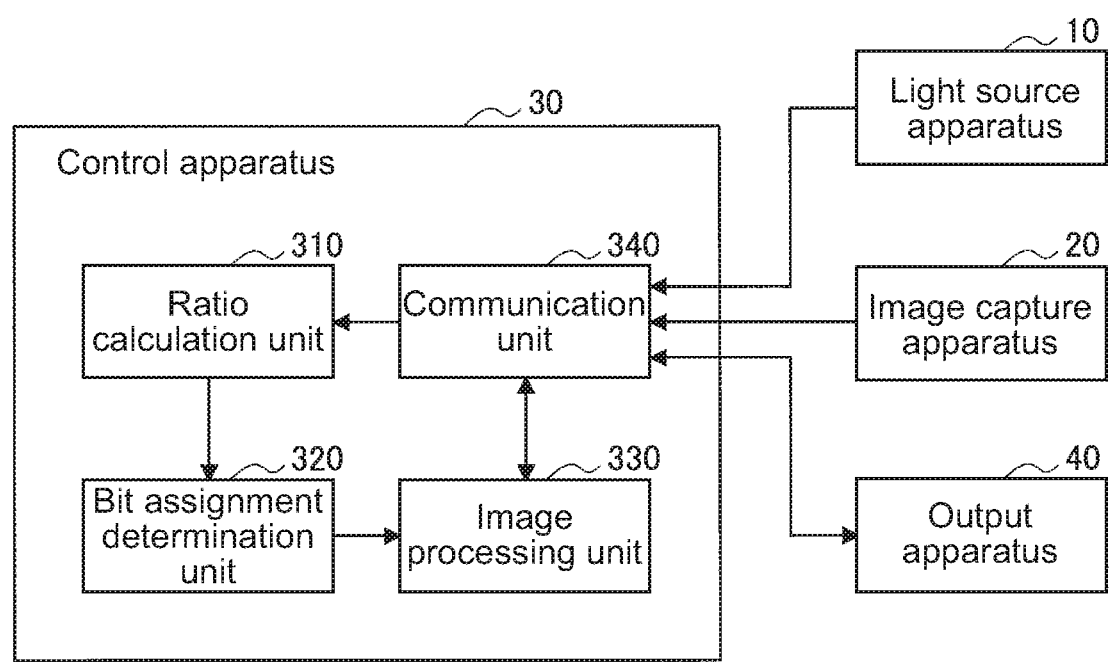
FIG. 6 is a functional block diagram of a control apparatus according to the embodiment.

Next, the functional configuration example of the control apparatus 30 according to the present embodiment will be described. FIG. 6 is a functional block diagram of the control apparatus 30 according to the embodiment. With reference to FIG. 6, the control apparatus 30 according to the present embodiment includes a ratio calculation unit 310, a bit assignment determination unit 320, an image processing unit 330, and a communication unit 340.

(Ratio Calculation Unit 310)

The ratio calculation unit 310 has a function to calculate the first ratio of the bit assignment relating to the transmission of the biological image on the basis of the image capture conditions. Here, the image capture conditions according to the present embodiment may include an image capture target in addition to the above-described image capture mode. The above-described image capture target may include a variety of information capable of specifying characteristics of light used for the image capture such as a surgery content and a usage of the biological image, for example. In this case, the ratio calculation unit 310 according to the present embodiment can estimate the image capture mode on the basis of the above-described image capture target.

Note that the ratio calculation unit 310 according to the present embodiment may calculate the above-described first ratio on the basis of the image capture conditions dynamically sent from the light source apparatus 10 or the image capture apparatus 20 and the image capture conditions inputted by the user such as the surgeon and the assistant. By the above-described function included in the ratio calculation unit 310 according to the present embodiment, it becomes possible to calculate the ratio of the bit assignment suitable to the image capture conditions of the biological image.

In addition, the ratio calculation unit 310 according to the present embodiment has a function to calculate a second ratio relating to the above-described bit assignment on the basis of the output characteristics of the output apparatus 40 that outputs the biological image. Here, the output characteristics according to the present embodiment may include a tone, a color gamut, brightness (nit), a gamma value, and the like corresponding to the output apparatus 40. In addition, the output characteristics according to the present embodiment can include a variety of information about the output apparatus 40, i.e., the output apparatus 40 is a monochrome monitor, for example.

Note that the ratio calculation unit 310 according to the present embodiment may calculate the above-described second ratio the basis of the image capture conditions dynamically sent from the output apparatus 40 and the output characteristics inputted by the user such as the surgeon and the assistant. By the above-described function included in the ratio calculation unit 310 according to the present embodiment, it becomes possible to calculate the ratio of the bit assignment suitable to the image capture conditions of the output apparatus 40.

(Bit Assignment Determination Unit 320)

The bit assignment determination unit 320 has a function to determine the bit assignment relating to the transmission of the biological image on the basis of the first ratio and the second ratio calculated by the ratio calculation unit 310. In this case, the bit assignment determination unit 320 according to the present embodiment may determine the bit assignment only on the basis of either the first ratio or the second ratio or may determine the bit assignment on the basis of both the first ratio and the second ratio.

In addition, the bit assignment determination unit 320 according to the present embodiment can also determine the bit assignment relating to the transmission of the biological image on the basis of a product of the first ratio and the second ratio. The functions of the ratio calculation unit 310 and the bit assignment determination unit 320 according to the present embodiment will be separately described.

(Image Processing Unit 330)

The image processing unit 330 has a function to perform image processing relating to the biological image on the basis of the bit assignment determined by the bit assignment determination unit 320. Specifically, the image processing unit 330 according to the present embodiment has a function to change the RAW signal transmitted from the image capture apparatus 20 into the bit assignment. By the above-described function included in the image processing unit 330 according to the present embodiment, it becomes possible to efficiently utilize a limited band and to prevent an image quality from being degraded due to the limitation by the transmission standard.

In addition, the image processing unit 330 according to the present embodiment may perform the image processing relating to the biological image on the basis of the gamma value of the output apparatus 40. More specifically, the image processing unit 330 according to the present embodiment can perform gamma compression based on the gamma value of the output apparatus 40 acquired in advance. Here, the above-described gamma compression may be correction (inverse gamma) with respect to the gamma value of the output apparatus 40. By the above-described function included in the image processing unit 330 according to the present embodiment, it becomes possible to realize the transmission of the signal suitable to the gamma value of the output apparatus 40 in advance.

(Communication Unit 340)

The communication unit 340 has a function to transmit the biological image processed by the image processing unit 330 and the information about the bit assignment determined by the bit assignment determination unit to the output apparatus 40. In addition, the communication unit 340 according to the present embodiment may receive the information about the image capture conditions from the light source apparatus 10 or the image capture apparatus 20 being connected. In addition, the communication unit 340 according to the present embodiment receives the information about the output characteristics such as the color gamut and the gamma value from the output apparatus 40 being connected.

The functional configuration example of the control apparatus 30 according to the present embodiment is described above. Note that the above-described configuration described by using FIG. 6 is just illustrative and the functional configuration of the control apparatus 30 according to the present embodiment is not limited thereto. The above-described functions included in the control apparatus 30 may be realized by distributing to a plurality of apparatuses. For example, the ratio calculation unit 310, the bit assignment determination unit 320, and the image processing unit 330 can be realized as functions of separate apparatuses. In addition, the control apparatus 30 may further include configurations other than those described by using FIG. 6. The functional configuration of the control apparatus 30 according to the present embodiment can be flexibly deformed.

<<1.6. Output Apparatus 40>>

Figure 7:
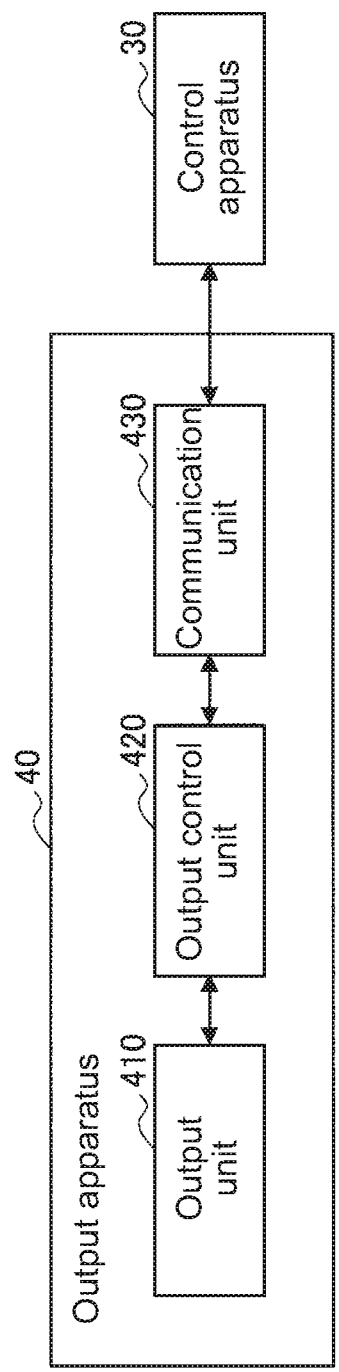
FIG. 7 is a functional block diagram of an output apparatus according to the embodiment.

Next, a functional configuration example of the output apparatus 40 according to the present embodiment will be described. FIG. 7 is the functional block diagram of the output apparatus according to the embodiment. With reference to FIG. 7, the output apparatus 40 according to the present embodiment includes an output unit 410, an output control unit 420, and a communication unit 430.

(Output Unit 410)

The output unit 410 has a function to output the biological image on the basis of the control by the output control unit 420. Therefore, the output unit 410 according to the present embodiment can be realized by including a display device such as a Liquid Crystal Display (LCD) apparatus and an OLED (Organic Light Emitting Diode) apparatus. In addition, the output unit 410 according to the present embodiment may be configured by including a variety of printing devices.

(Output Control Unit 420)

The output control unit 420 has a function to cause the output unit 410 to output the biological image. In this case, the output control unit 420 according to the present embodiment can cause the output unit 410 to output with an adequate tone and a color gamut on the basis of the information about the bit assignment transmitted together with the above-described biological image.

(Communication Unit 430)

The communication unit 430 has a function to perform information communication with the control apparatus 30. Specifically, the communication unit 430 according to the present embodiment receives the information about the biological image and the bit assignment from the control apparatus 30. In addition, communication unit 430 according to the present embodiment sends the information about the output characteristics to the control apparatus 30. In this case, the communication unit 430 can dynamically send the information about the output characteristics the control apparatus 30 on the basis that the communication with the control apparatus 30 is ensured.

The functional configuration example of the output apparatus 40 according to the present embodiment is described above. Note that the above-described configuration described by using FIG. 7 is just illustrative and the functional configuration of the output apparatus 40 according to the present embodiment is not limited thereto. The functional configuration of output apparatus 40 according to the present embodiment can be flexibly deformed.

<<1.7. Details of Bit Assignment>>

Next, details of the bit assignment relating to the present embodiment will be described with specific examples.

(Calculation of First Ratio)

First, calculating the first ratio according to the present embodiment will be described in detail. As described above, the ratio calculation unit 310 according to the present embodiment can calculate the first ratio of the bit assignment relating to the transmission of the biological image on the basis of the image capture conditions including the image capture mode and the like. For example, in a case of the biological image is captured for an endoscopic observation, the color gamut to be outputted is often limited depending on purposes of a therapy, an observation, and the like. Therefore, in a case where the above-described biological image is transmitted, a bit expression is not necessarily limited to equal in 3ch.

Figure 8:
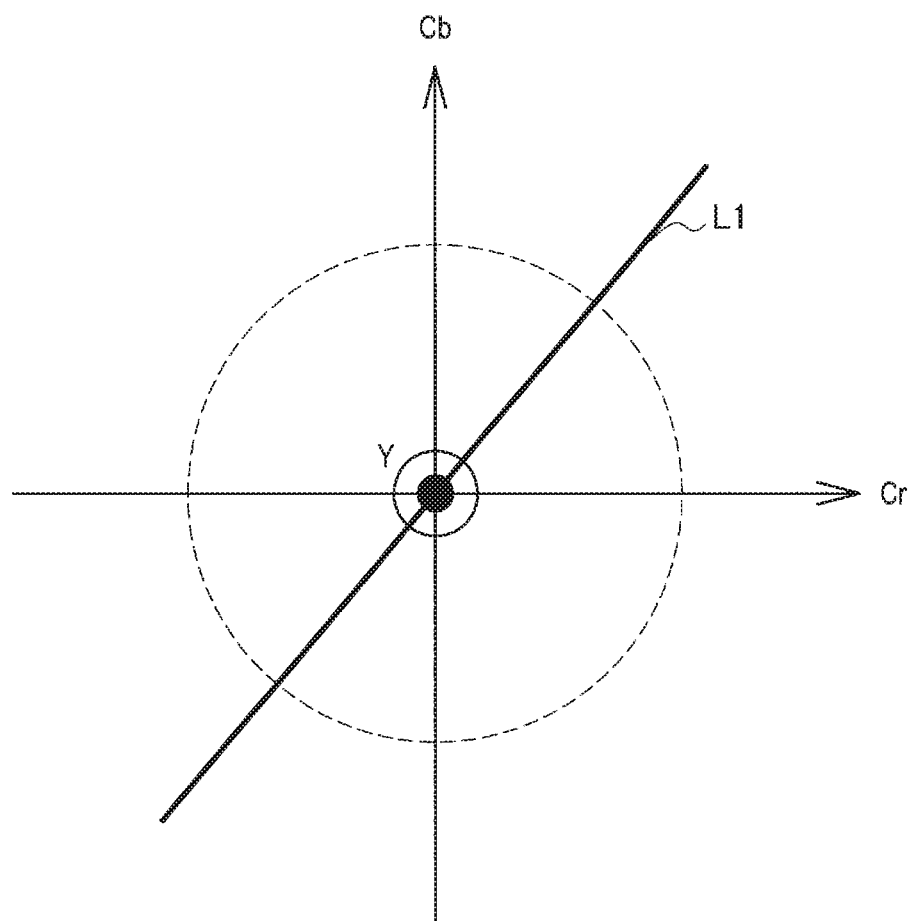
FIG. 8 is a diagram showing a color distribution on one plane in a color space in a case where a component of R or B is not used according to the embodiment.

FIG. 8 is a diagram showing a color distribution on one plane in a color space in a case where a component of R or B is not used. As shown in FIG. 8, in a case where the component of R or B is not used, it is possible to two-dimensionally express a coordinate on the color space. Therefore, the coordinate in the color space on a certain plane can be expressed by a linear expression as a solid line L1 shown in FIG. 8. For example, since the component of R of the color information is not used in the narrow band imaging, the ratio calculation unit 310 according to the present embodiment can improve quantization precision of the signal by increasing the ratio of the components of G and B.

In addition, for example, in a case where the biological image captured in the auto fluorescence imaging is transmitted, as the color information is not used for the output, it is desirable to assign all bands to a brightness component. In this case, the ratio calculation unit 310 according to the present embodiment can calculate the first ratio having a greater bias to the brightness component.

Note that, in this case, the ratio calculation unit 310 according to the present embodiment may calculate the first ratio on the basis of image capture mode information dynamically sent from the light source apparatus 10 or the image capture apparatus 20, or may calculate the first ratio on the basis of image capture mode information inputted and set by the user such as the surgeon.

In addition, as described above, the ratio calculation unit 310 according to the present embodiment may estimate the image capture mode on the basis of the image capture target such as the surgery content and the usage of the biological image and may calculate the first ratio. The ratio calculation unit 310 can estimate the image capture mode on the basis of the image capture target inputted and set, for example, by the user such as the surgeon and the image capture target sent from an external apparatus. As an example, the ratio calculation unit 310 according to the present embodiment may estimate the image capture mode as the narrow band imaging mode on the basis that the surgery content is an observation of an early lesion such as a cancer.

In addition, the ratio calculation unit 310 can also calculate the first ratio depending on the characteristics of each biological image on the basis that the captured biological image is finally superimposed-processed. In this case, the ratio calculation unit 310 may calculate the first ratio on the basis of the usage inputted by the user such as the surgeon, for example.

In addition, the ratio calculation unit 310 can also calculate the first ratio on the basis of a color difference acquired from the image capture apparatus 20 and the information about a minimum value, a maximum value, or the like of the signal component. The ratio calculation unit 310 may calculate the first ratio to focus on more important information by removing the signal component that is estimated as unnecessary from the above-described information.

(Calculation of Second Ratio)

Next, calculating the first ratio according to the present embodiment will be described in detail. The ratio calculation unit 310 according to the present embodiment can calculate the second ratio of the bit assignment relating to the transmission of the biological image on the basis of the output characteristics of the output apparatus 40. For example, a medical monitor used in the endoscope system often has high color reproducibility and color gamut as compared with a general monitor. However, in fact, due to the limitation by the transmission standard as described above, it is even seen that the performance cannot be sufficiently utilized.

Figure 9:
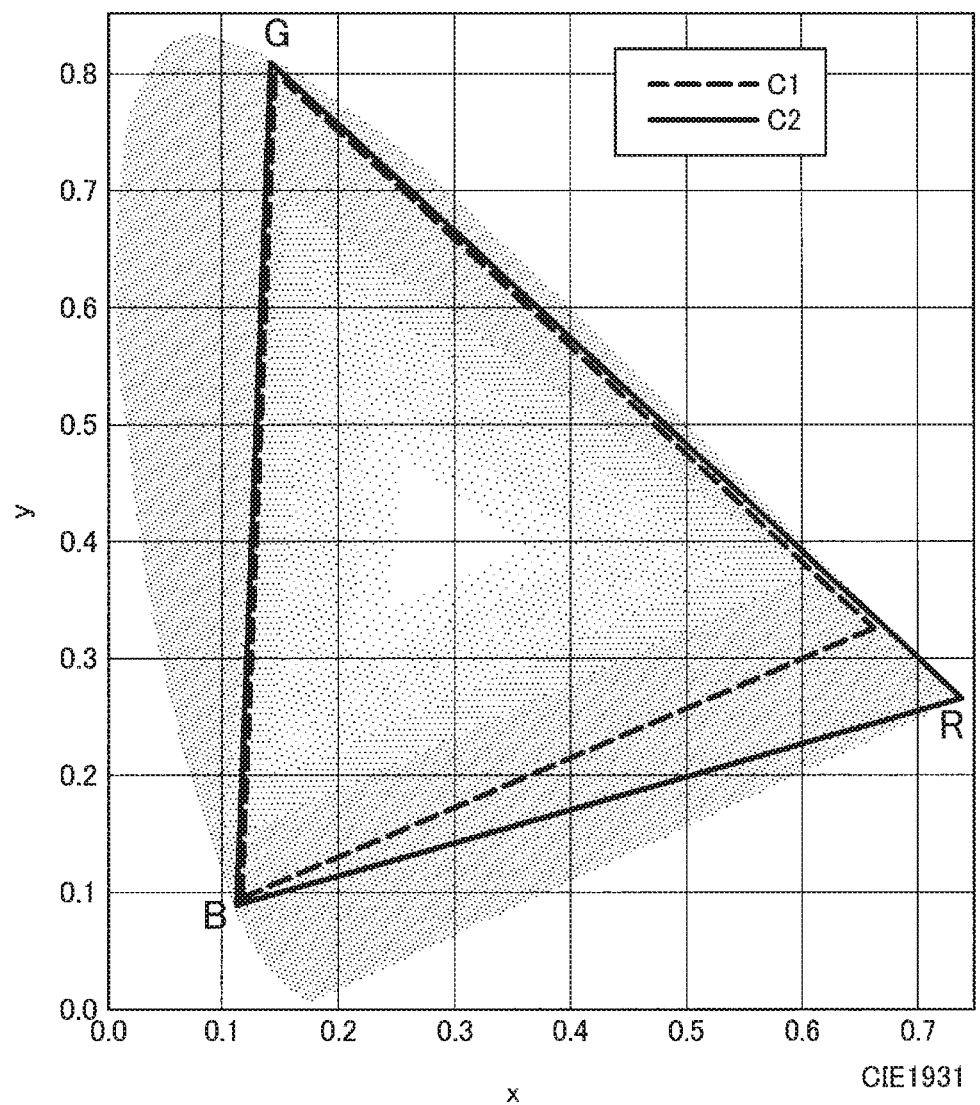
FIG. 9 is a diagram for describing a color gamut relationship between a certain transmission standard X and a monitor Y and according to the embodiment.

FIG. 9 is a diagram for describing a color gamut relationship between a certain transmission standard X and a monitor Y. FIG. 9 shows a color gamut C1 supported by the transmission standard X and a color gamut C2 that can be expressed on a monitor Y. Here, as shown FIG. 9, even if the color gamut of R that can be expressed on the monitor Y is wider than the color gamut of the standard X, the standard X is identified by the monitor Y and the color gamut more than the standard X is thus not expressed on the monitor Y.

In addition, depending on the monitor, it is also envisioned that the signal is scaled at the monitor. In this case, a contrast resolution will be decreased.

Therefore, the ratio calculation unit 310 according to the present embodiment may calculate the second ratio relating to the transmission of the biological image on the basis of the color gamut that can be expressed by the output apparatus 40 and the color gamut supported by the transmission standard. Specifically, in the case of the example shown in FIG. 9, the ratio calculation unit 310 according to the present embodiment can cover the color gamut corresponding to the characteristics of the output apparatus 40 by increasing the ratio relating to R.

In this case, the ratio calculation unit 310 according to the present embodiment may calculate the second ratio on the basis of the information of the color gamut dynamically sent from the output apparatus 40 or may calculate the second ratio based on the color gamut of the output apparatus 40 on the basis of the information of the output apparatus 40 inputted and set by the user such as the surgeon.

(Specific Example of Bit Assignment Relating to White Light Imaging)

Figure 10:
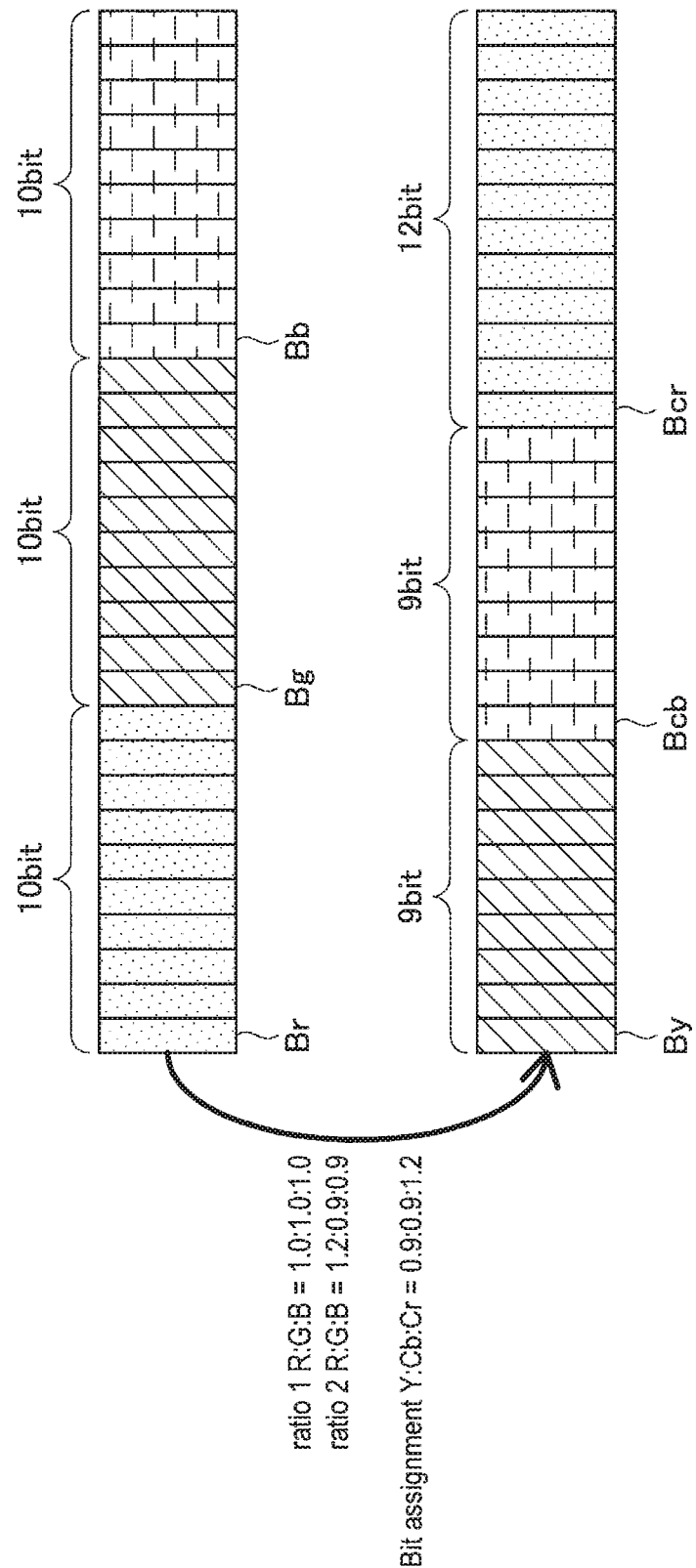
FIG. 10 is a diagram for describing a specific example of a bit assignment relating to white light imaging in the embodiment.

Next, a specific example of the bit assignment in a case where the image capture mode is the white light imaging mode will be described. FIG. 10 is a diagram for describing the specific example of the bit assignment relating to the white light imaging.

In the white light imaging, since the biological image is captured by white light irradiated from the light source apparatus 10, the output apparatus 40 performs output by using color information of all of red, green, and blue. Therefore, in the case where the image capture mode is the white light imaging mode, the ratio calculation unit 310 according to the present embodiment may calculate the first ratio such that the signal components of red, green, and blue may be equal as shown in FIG. 10. Specifically, the ratio calculation unit 31 according to the present embodiment can calculate the first ratio to be R:G:B=1.0:1.0:1.0.

On the other hand, the ratio calculation unit 310 according to the present embodiment can calculate the second ratio depending on the color gamut of the output apparatus 40, even in the white light imaging. For example, in a case where the color gamut supported by the transmission standard and the color gamut that can be expressed by the output apparatus 40 are the color gamut C1 and the color gamut C2 respectively shown in FIG. 9, the ratio calculation unit 310 may calculate the second ratio having the increased ratio relating to R. The ratio calculation unit 310 may have the second ratio, for example, to be R:G:B=1.2:0.9:0.9 as shown in FIG. 10.

In this case, the bit assignment determination unit 320 according to the present embodiment can determine the bit assignment relating to the transmission of the biological image on the basis of the first ratio and the second ratio calculated by the ratio calculation unit 310. The bit assignment determination unit 320 may determine the above-described bit assignment, for example, on the basis of a product of the first ratio and the second ratio.

In addition, in this case, the bit assignment determination unit 320 according to the present embodiment may convert the bit assignment based on RGB transmitted from the image capture apparatus 20 into the bit assignment based on YCbCr. The bit assignment determination unit 320 may perform the above-described conversion on the basis of a conversion expression for each transmission standard set in advance. In the example shown in FIG. 10, the bit assignment determination unit 320 according to the present embodiment determines the bit assignment as Y:Cb:Cr=0.9:0.9:1.2 on the basis of the first ratio, the second ratio, and the above-described conversion expression. Here, the bit By denotes a bit corresponding to a brightness (Y) signal, the bit Bcb denotes a bit corresponding to a blue color difference (Cb) signal in FIG. 10. In addition, the bit Bcr denotes a bit corresponding to a red color difference (Cr) signal in FIG. 10.

(Specific Example of Bit Assignment Relating to Narrow Band Imaging)

Figure 11:
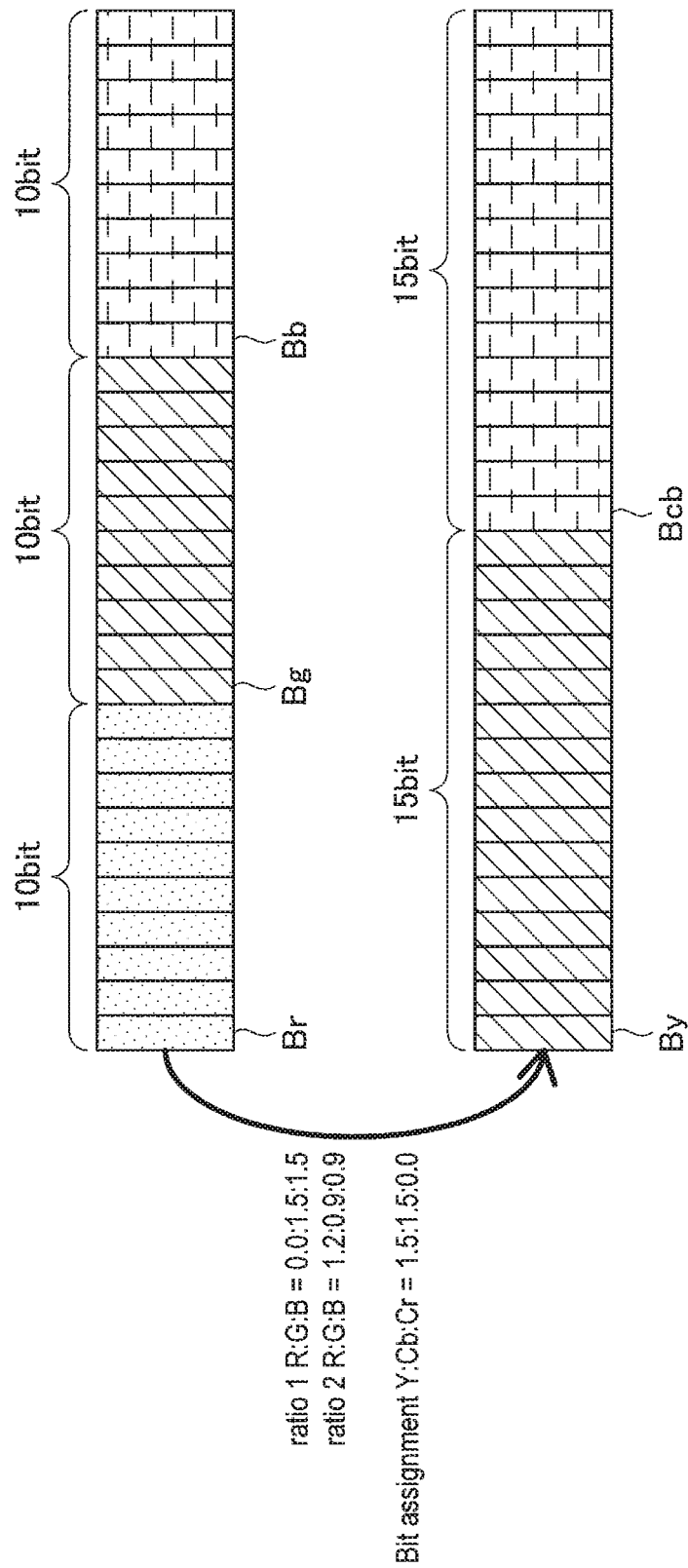
FIG. 11 is a diagram for describing a specific example of a bit assignment relating to narrow band imaging in the embodiment.

Next, a specific example of the bit assignment in a case where the image capture mode is the narrow band imaging mode will be described. FIG. 11 is a diagram for describing the specific example of the bit assignment relating to the narrow band imaging.

As described above, in the narrow band imaging, since the biological image is captured by the wavelengths of green and blue light irradiated from the light source apparatus 10, the output apparatus 40 does not need color information about red. Therefore, the ratio calculation unit 310 according to the present embodiment may calculate the first ratio such that a ratio of signal components of color information about irradiation light upon image capture is increased in a case where the image capture mode is a narrow band imaging mode. Specifically, the ratio calculation unit 310 according to the present embodiment can calculate the first ratio to be R:G:B=0.0:1.5:1.5.

In addition, the calculation unit 310 according to the present embodiment ratio may calculate the second ratio depending on the color gamut of the output apparatus 40, even in the narrow band imaging. In the case of the example shown in FIG. 11, the ratio calculation unit 310 may have the second ratio of R:G:B=1.2:0.9:0.9 similar to the case described by using FIG. 10.

In addition, the bit assignment determination unit 320 according to the present embodiment determines the bit assignment relating to the transmission of the biological image on the basis of the first ratio and the second ratio calculated as described above similar to the case of the white light imaging. In the case of the example shown in FIG. 11, the bit assignment determination unit 320 according to the present embodiment determines the bit assignment to be Y:Cb:Cr=1.5:1.5:0.0 on the basis of the first ratio and the second ratio.

(Specific Example of Bit Assignment Relating to Auto Fluorescence Imaging)

Figure 12:
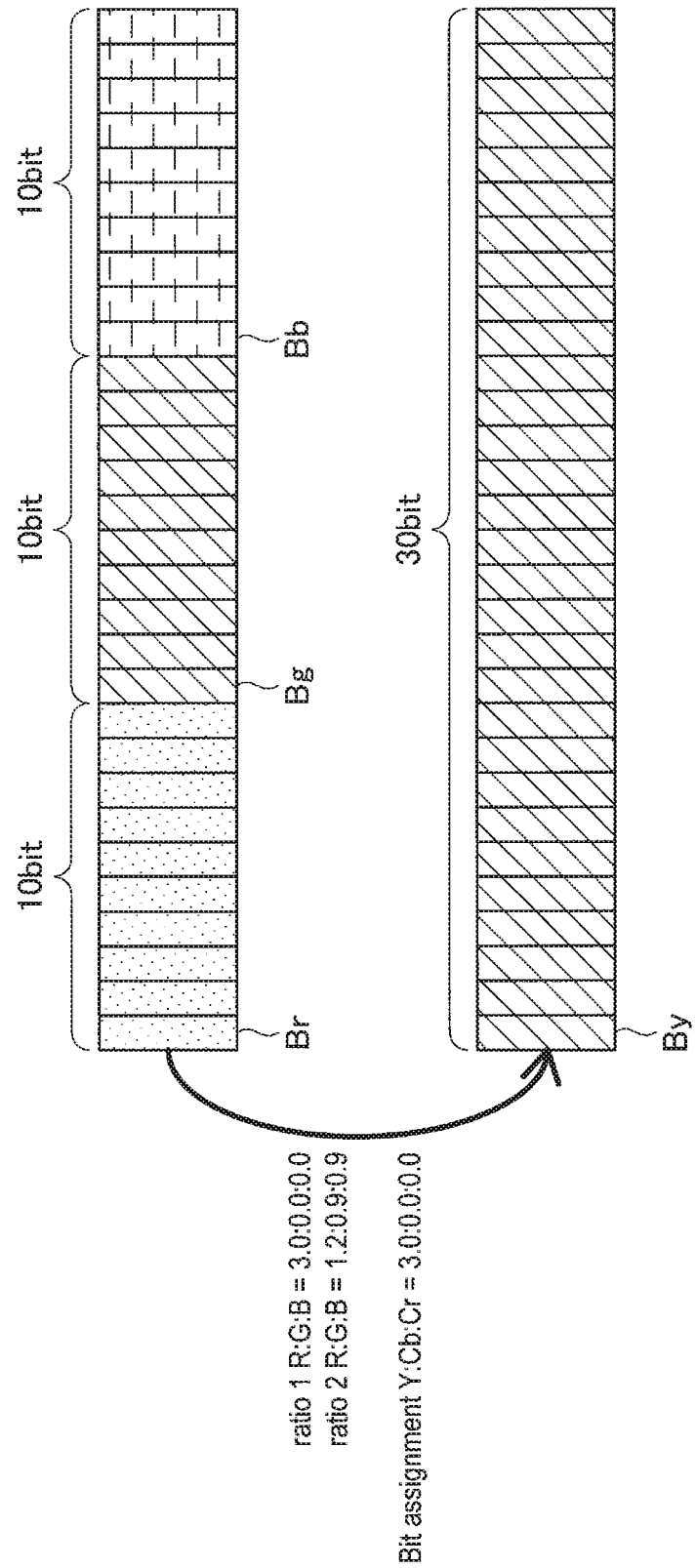
FIG. 12 is a diagram for describing a specific example of a bit assignment relating to auto fluorescence imaging in the embodiment.

Next, a specific example of the bit assignment in a case where the image capture mode is the auto fluorescence imaging mode will be described. FIG. 12 is a diagram for describing the specific example of the bit assignment relating to the auto fluorescence imaging.

As described above, in a case where the biological image captured in the auto fluorescence imaging is transmitted, as the color information is not used for the output by the output apparatus 40, it is desirable to assign all bands to the brightness component. Therefore, the ratio calculation unit 310 according to the present embodiment may calculate the first ratio such that a ratio of signal components of brightness information is increased in a case where the image capture mode is the auto fluorescence imaging mode. Specifically, the ratio calculation unit 310 according to the present embodiment can calculate the first ratio to be R:G:B=3.0:0.0:0.0. Note that since R=G=B in the auto fluorescence imaging, any one of R, G, and B may be 3.0.

In addition, the ratio calculation unit 310 according to the present embodiment may calculate the second ratio depending on the color gamut of the output apparatus 40 also in the case of the auto fluorescence imaging. In the case of the example shown in FIG. 12, the ratio calculation unit 310 may have the second ratio of R:G:B=1.2:0.9:0.9 similar to the case described by using FIG. 10.

In addition, the bit assignment determination unit 320 according to the present embodiment determines the bit assignment relating to the transmission of the biological image on the basis of the first ratio and the second ratio calculated as described above similar to the case of the white light imaging and the narrow band. In the case of the example shown in FIG. 12, the bit assignment determination unit 320 according to the present embodiment determines the bit assignment as Y:Cb:Cr=3.0:0.0:0.0 on the basis of the first ratio and the second ratio.

<<1.8. Operation Flow of Control Apparatus 30>>

Figure 13:
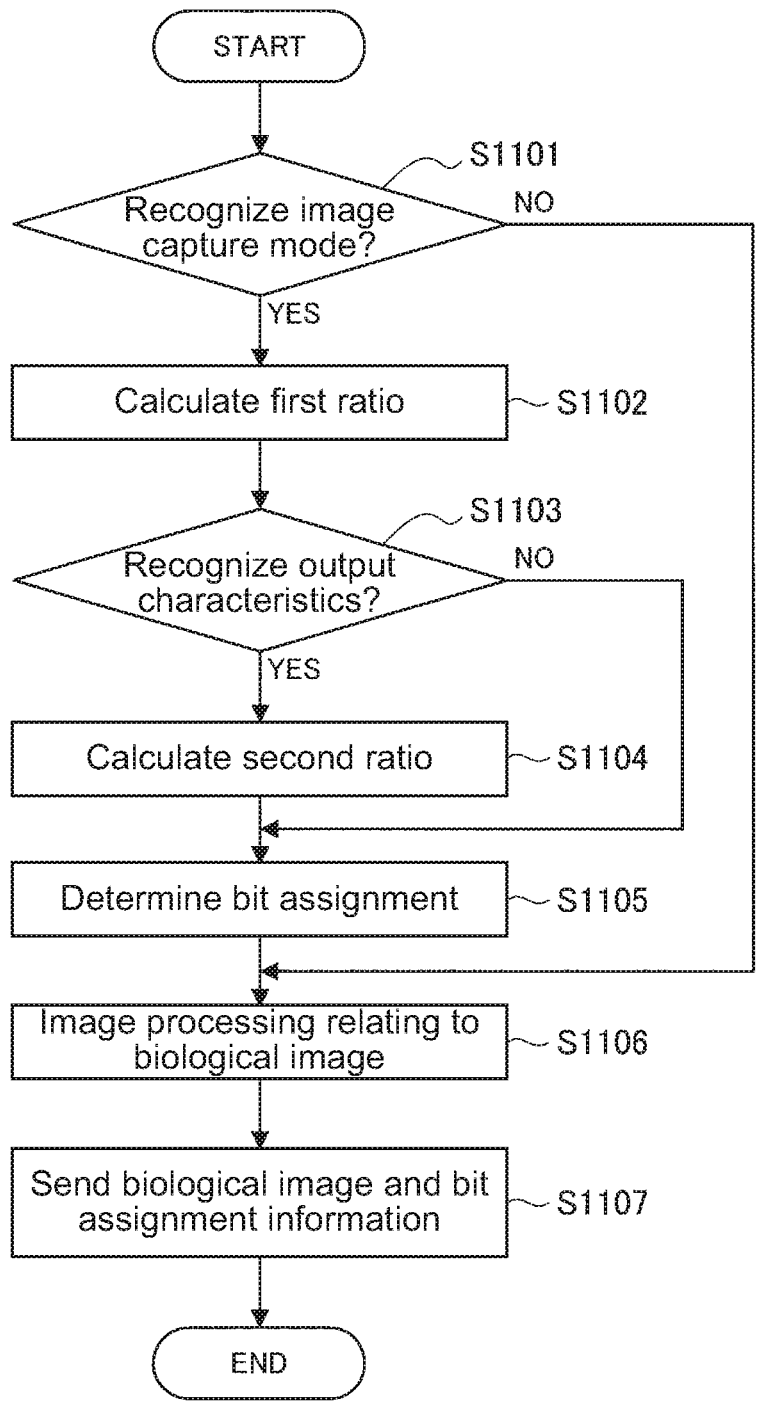
FIG. 13 is a flowchart showing an operation flow of a control apparatus according to the embodiment.

Next, an operation flow of the control apparatus 30 according to the present embodiment will be described in detail. FIG. 13 is a flowchart showing the operation flow of the control apparatus according to the embodiment.

With reference to FIG. 13, the ratio calculation unit 310 of the control apparatus 30 first recognizes the image capture mode (S1101). In this case, the ratio calculation unit 310 may recognize the image capture mode on the basis of the information dynamically sent from the light source apparatus 10 or the image capture apparatus 20 or may estimate the image capture mode also on the basis of the image capture target inputted and set by the user such as the surgeon.

Here, if the ratio calculation unit 310 cannot recognize the image capture mode (S1101: NO), the control apparatus 30 skips processing relating to determination of the bit assignment (S1102 to S1105).

On the other hand, if the ratio calculation unit 310 recognizes the image capture mode (S1101: YES), the ratio calculation unit 310 subsequently calculates the first ratio relating to the bit assignment on the basis of the image capture mode recognized in Step S1101 (S1102).

Subsequently, the ratio calculation unit 310 recognizes the output characteristics of the output apparatus 40 (S1103). In this case, the ratio calculation unit 310 may recognize the output characteristics such as the color gamut on the basis of the information dynamically sent from the output apparatus 40 or may recognize the output characteristics also on the basis of the information inputted and set by the user such as the surgeon.

Here, if the ratio calculation unit 310 cannot recognize the output characteristics of the output apparatus 40 (S1103: NO), the control apparatus 30 skips processing relating to the calculation of the second ratio (S1104).

On the other hand, if the ratio calculation unit 310 recognizes the output characteristics of the output apparatus 40 (S1103: YES), the ratio calculation unit 310 subsequently calculates the second ratio relating to the bit assignment on the basis of the output characteristics recognized in Step S1103 (S1104).

Next, the bit assignment determination unit 320 determines the bit assignment relating to the transmission of the biological image on the basis of the first ratio calculated in Step S1102 and the second ratio calculated in Step S1104 (S1105). Note that, in this case, if the second ratio is not calculated in Step S1104, the bit assignment determination unit 320 may determine the above-described bit assignment only on the basis of the first ratio.

Next, the image processing unit 330 performs image processing relating to the biological image on the basis of the bit assignment determined in Step S1104 (S1106). In addition, the image processing unit 330 may perform gamma compression or the like based on the gamma value recognized in Step S1103.

Next, the communication unit 340 transmits the biological image processed in Step S1106 and the information about the bit assignment determined in Step S1105 to the output apparatus 40 (S1107). The output apparatus 40 according to the present embodiment can output the biological image corresponding to the image capture mode and the output characteristics on the basis of the biological image transmitted in Step S1106 and the information about the bit assignment.

<2. Hardware Configuration Example>

Figure 14:
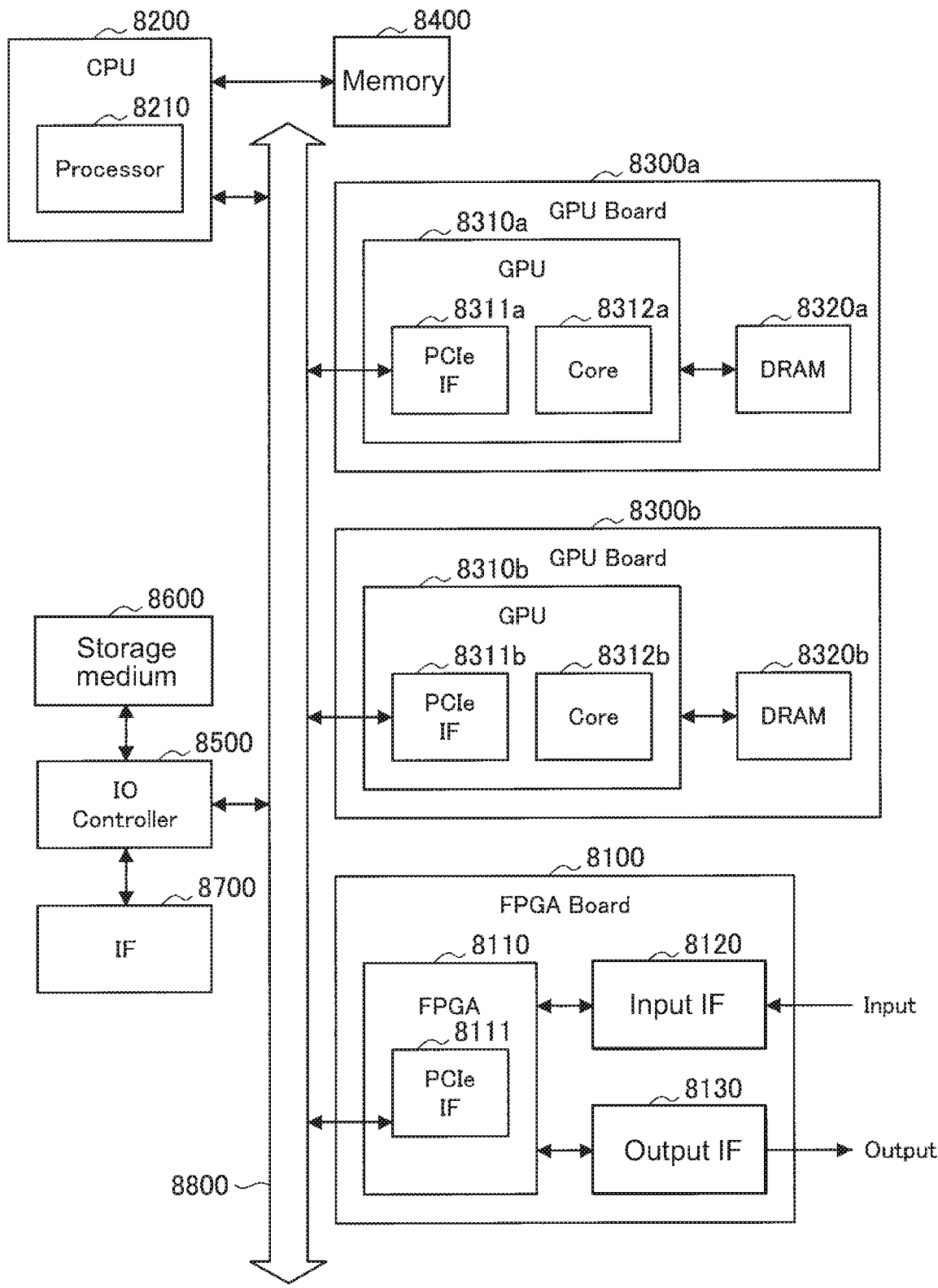
FIG. 14 is a hardware configuration example according to the control apparatus of the present disclosure.

Next, a hardware configuration example of the control apparatus 30 according to the present disclosure will be described. FIG. 14 is a block diagram showing a hardware configuration example of the control apparatus 30 according to the present disclosure. With reference to FIG. 14, the control apparatus 30 includes an FPGA board 8100, a CPU 8200, a GPU board 8300, a memory 8400, an IO controller 8500, a recording medium 8600, and an interface 8700. In addition, the FPGA board 8100, the CPU 8200, the GPU board 8300, and the IO controller 8500 are connected via a bus 8800.

(FPGA Board 8100)

The FPGA board 8100 is configured by including an FPGA 8110, an interface 8120 to which an input image signal is inputted from the input image capture apparatus 20, an output interface 8130 that outputs an output image signal to the output apparatus 40, and the like, for example. In addition, the FPGA 8110 is connected to the bus 8800 through a PCIe interface 8111.

(CPU 8200)

The CPU 8200 is configured by including a processor 8210 and functions as the calculation processing apparatus or the control apparatus, for example. The CPU 8200 may control reading and writing of data stored in the memory 8400, for example. In addition, the CPU 8200 may divide image data stored in the memory 8400 depending on a processing capability and a processing content of the GPU board 8300. In this case, a processing result of the GPU board 8300 with respect to the divided image data is inputted to the CPU 8200.

(GPU Board 8300)

The GPU board 8300 executes, for example, a variety of software such as relevant software and performs a variety of processing. The GPU board 8300 is configured by including a GPU (Graphics Processing Unit) 8310 and a DRAM (Dynamic Random Access Memory) 8320. In addition, the GPU 8312 includes a PCIe interface 8311 connecting to the bus and a core 8312. Note that although FIG. 14 shows an example that the control apparatus 30 includes two GPU boards 8300a and 8300b, the control apparatus 30 may include three or more GPUs 8300. On the other hand, if the CPU 8200 has an equivalent function as the GPU 8312, the control apparatus 30 may not include the GPU board 8300.

(Memory 8400)

A variety of data such as data corresponding to the input image signal from the image capture apparatus 20 and data corresponding to the output image signal to the output apparatus 40 are stored in the memory 8400. In addition, a variety of programs, data used for calculation, and the like are stored in the memory 8400.

(IO Controller 8500)

The IO controller 8500 has a function to control signal transmission among the CPU 8200, the recording medium 8600, and the interface 8700, for example.

(Recording Medium 8600)

The recording medium 8600 functions as a storage unit and records a variety of data such as image data and a variety of applications. Examples of the recording medium 8600 include a solid state drive, for example. In addition, the recording medium 8600 may be attachable and detachable to/from the control apparatus 30.

(Interface 8700)

Examples of the interface 8700 includes a USB (Universal Serial Bus) terminal and a processing circuit, a LAN (Local Area Network) terminal and a sending and receiving circuit, and the like, for example.

As described above, the hardware configuration example of the control apparatus 30 according to the present disclosure is described. Note that the above-described configuration described by using FIG. 14 is just illustrative and a part of the components may be omitted. In addition, the control apparatus 30 may further include components other than those described above.

<3. Summary>

As described above, the control apparatus 30 according to the present disclosure can calculate the first ratio of the bit assignment relating to the transmission of the biological image on the basis of the image capture conditions. In addition, the control apparatus 30 according to the present disclosure can calculate the second ratio of the bit assignment relating to the transmission on the basis of the output characteristics of the output apparatus 40. In addition, the control apparatus 30 according to the present disclosure can determine the bit assignment relating to the transmission of the biological image on the basis of the above-described first ratio and the second ratio. According to the configuration, it becomes possible to realize the transmission of the biological image suitable to the image capture conditions and the characteristics of the output apparatus.

While the present disclosure is described in detail with reference to attached drawings about preferable embodiments, the technical scope of the present disclosure is not limited thereto. It is apparent that those having ordinary skill in the art of the present disclosure may conceive a variety of variations and modifications within the scope of the technical spirit described in the claims. It should be appreciated that they are belong to the technical scope of the present disclosure.

In addition, each step in the processing of the control apparatus 30 in the present specification is not necessarily performed in time series along the order described in the flowchart. For example, each step in the processing of the control apparatus 30 may be performed in the order different from the described order or may be performed in parallel.

In addition, effects described herein are just explanatory and illustrative and are not limited. In other words, the technology according to the present disclosure can exhibit other effects apparent to those skilled in the art from the description of the present specification together with the above-described effects or in place of the above-described effects.

Note that the following structures also belong to a technical scope of the present disclosure.

(1)

A control apparatus, including:

a ratio calculation unit calculating a first ratio of a bit assignment relating to transmission of a biological image on a basis of image capture conditions; and a bit assignment determination unit determining the bit assignment on a basis of the first ratio.

(2)

The control apparatus according to (1), in which the image capture conditions include an image capture mode.

(3)

The control apparatus according to (2), in which the image capture mode includes a white light imaging mode, a narrow band imaging mode, and an auto fluorescence imaging mode.

(4)

The control apparatus according to (2) or (3), in which the image capture conditions include an image capture target, and the ratio calculation unit estimates the image capture mode on a basis of the image capture target.

(5)

The control apparatus according to any of (2) to (4), in which the ratio calculation unit calculates the first ratio such that a ratio of signal components of color information about irradiation light upon image capture is increased in a case where the image capture mode is a narrow band imaging mode.

(6)

The control apparatus according to any of (2) to (5), in which the ratio calculation unit calculates the first ratio such that a ratio of signal components relating to brightness information is increased in a case where the image capture mode is an auto fluorescence imaging mode.

(7)

The control apparatus according to any of (1) to (6), in which the ratio calculation unit calculates a second ratio relating to the bit assignment on a basis of output characteristics of an output apparatus outputting the biological image, and the bit assignment determination unit determines the bit assignment further on a basis of the second ratio.

(8)

The control apparatus according to (7), in which the output characteristics include a color gamut, and the ratio calculation unit calculates the second ratio on a basis of the color gamut.

(9)

The control apparatus according to (8), in which the ratio calculation unit calculates the second ratio further on a basis of a color gamut of a transmission standard relating to transmission of the biological image.

(10)

The control apparatus according to any of (7) to (9), in which the bit assignment determination unit determines the bit assignment on a basis of a product of the first ratio and the second ratio.

(11)

The control apparatus according to any of (1) to (10), further including:

an image processing unit performing image processing relating to the biological image on a basis of the bit assignment.

(12)

The control apparatus according to (11), in which the image processing unit performs image processing relating to the biological image further on a basis of a gamma value of an output apparatus outputting the biological image.

(13)

The control apparatus according to any of (1) to (12), further including:

a communication unit transmitting information about the biological image and the bit assignment.

(14)

The control apparatus according to (13), in which the communication unit receives information about the image capture conditions from a light source apparatus or an image capture apparatus being connected.

(15)

The control apparatus according to (13) or (14), in which the communication unit receives information about output characteristics of an output apparatus from the output apparatus being connected.

(16)

A control system, including:

an image capture apparatus including an image capture unit capturing an object;

a control apparatus including a ratio calculation unit calculating a first ratio of a bit assignment relating to transmission of a biological image on a basis of image capture conditions relating to the object, a bit assignment determination unit determining the bit assignment on a basis of the first ratio, and an image processing unit performing image processing based on an image captured by the image capture unit and the bit assignment and generating the biological image; and an output apparatus including an output unit performing an output relating to the biological image based on the bit assignment.

(17)

The control system according to (16), further including:

a light source apparatus including an irradiation unit irradiating the object with light in an image capture of the object by the image capture unit.

(18)

The control system according to (17), in which the image capture conditions include an image capture mode relating to image capture of the object, the control apparatus further includes a communication unit receiving information about the image capture mode from the image capture apparatus or the light source apparatus, and the ratio calculation unit calculates the first ratio on a basis of the image capture mode.

(19)

The control system according to (18), in which the communication unit receives information about output characteristics of the output apparatus, the ratio calculation unit calculates a second ratio relating to the bit assignment on a basis of the output characteristics, and the bit assignment determination unit determines the bit assignment further on a basis of the second ratio.

(20)

A control method, including:

calculating a first ratio of a bit assignment relating to transmission of a biological image on a basis of image capture conditions by a processor; and determining the bit assignment on a basis of the first ratio by the processor.

(21)

A program to be executed as a control apparatus, including:

a ratio calculation unit calculating a first ratio of a bit assignment relating to transmission of a biological image on a basis of image capture conditions; and a bit assignment determination unit determining the bit assignment on a basis of the first ratio.

REFERENCE SIGNS LIST

10 light source apparatus
110 irradiation unit
120 irradiation control unit
130 communication unit
image capture apparatus
210 image capture unit
220 image capture control unit
230 communication unit
30 control apparatus
310 ratio calculation unit
320 bit assignment determination unit
330 image processing unit
340 communication unit
40 output apparatus
410 output unit
420 output control unit
430 communication unit
1000 control system

The invention claimed is:

1. A control apparatus, comprising:
a central processing unit (CPU) configured to:
calculate a first ratio of a bit assignment associated with transmission of a biological image, wherein
the first ratio is calculated based on at least one image capture condition of a plurality of image capture conditions,
the at least one image capture condition includes an image capture mode of the biological image,
the image capture mode is one of a narrow band imaging mode a white light imaging mode, or an auto fluorescence imaging mode,
the first ratio is of the bit assignment to a plurality of signal components of color information of irradiation light, and
the biological image is captured based on the irradiation light;
calculate a second ratio, associated with the bit assignment, based on a plurality of output characteristics of an output apparatus, wherein
the output apparatus:
receives the transmitted biological image, and
outputs the received biological image;
change the bit assignment based on the first ratio and the second ratio;
increase a value of the bit assignment for a specific signal component of the plurality of signal components of the irradiation light based on the change in the bit assignment; and
control the transmission of the biological image based on the increase in the value of the bit assignment for the specific signal component of the irradiation light.

2. The control apparatus according to claim 1, wherein
the plurality of image capture conditions includes an image capture target, and
the CPU is further configured to estimate the image capture mode based on the image capture target.

3. The control apparatus according to claim 1, wherein
the plurality of output characteristics includes a color gamut, and
the CPU is further configured to calculate the second ratio based on the color gamut.

4. The control apparatus according to claim 3, wherein the CPU is further configured to calculate the second ratio based on a color gamut of a transmission standard associated with the transmission of the biological image.

5. The control apparatus according to claim 1, wherein the CPU is further configured to determine the bit assignment based on a product of the first ratio and the second ratio.

6. The control apparatus according to claim 1, wherein the CPU is further configured to control execution of an image process, associated with the biological image, based on the bit assignment.

7. The control apparatus according to claim 6, wherein
the CPU is further configured to control the execution of the image process, associated with the biological image, based on a gamma value of the output apparatus.

8. The control apparatus according to claim 1, wherein the CPU is further configured to transmit information of the biological image and the bit assignment.

9. The control apparatus according to claim 8, wherein the CPU is further configured to receive information of the plurality of image capture conditions from at least one of a light source apparatus or an image capture apparatus.

10. The control apparatus according to claim 8, wherein the CPU is further configured to receive information of the plurality of output characteristics of the output apparatus from the output apparatus.

11. A control system, comprising:
an image capture apparatus configured to capture a biological image of an object based on irradiation light;
an output apparatus; and
a central processing unit (CPU) configured to:
calculate a first ratio of a bit assignment associated with transmission of the biological image, wherein
the first ratio is calculated based on at least one image capture condition of a plurality of image capture conditions associated with the object,
the at least one image capture condition includes an image capture mode of the capture of the biological image,
the image capture mode is one of a narrow band imaging mode a white light imaging mode, or an auto fluorescence imaging mode, and
the first ratio is of the bit assignment to a plurality of signal components of color information of the irradiation light;
calculate a second ratio, associated with the bit assignment, based on a plurality of output characteristics of the output apparatus;
change the bit assignment based on the first ratio and the second ratio;
increase a value of the bit assignment for a specific signal component of the plurality of signal components of the irradiation light based on the change in the bit assignment;
control execution of an image process based on the biological image and the bit assignment; and
control the transmission of the biological image based on the execution of the image process and the increase in the value of the bit assignment for the specific signal component of the irradiation light, wherein
the output apparatus is configured to:
receive the transmitted biological image; and
output the received biological image based on the bit assignment.

12. The control system according to claim 11, further comprising a light source apparatus configured to control irradiation of the object with the irradiation light in an image capture of the object.

13. The control system according to claim 12, wherein the CPU is further configured to receive information of the image capture mode from at least one of the image capture apparatus or the light source apparatus.

14. The control system according to claim 13, wherein the CPU is further configured to
receive information of the plurality of output characteristics of the output apparatus from the output apparatus.

15. A control method, comprising:
calculating a first ratio of a bit assignment associated with transmission of a biological image, wherein
the first ratio is calculated based on at least one image capture condition of a plurality of image capture conditions,
the at least one image capture condition includes an image capture mode of the biological image,
the image capture mode is one of a narrow band imaging mode, a white light imaging mode, or an auto fluorescence imaging mode,
the first ratio is of the bit assignment to a plurality of signal components of color information of irradiation light, and
the biological image is captured based on the irradiation light;
calculating a second ratio, associated with the bit assignment, based on a plurality of output characteristics of an output apparatus, wherein
the output apparatus:
receives the transmitted biological image, and
outputs the received biological image;
changing the bit assignment based on the first ratio and the second ratio;
increasing a value of the bit assignment for a specific signal component of the plurality of signal components of the irradiation light based on the change in the bit assignment; and
controlling the transmission of the biological image based on the increase in the value of the bit assignment for the specific signal component of the irradiation light.

16. A control apparatus, comprising:
a central processing unit (CPU) configured to:
calculate a first ratio of a bit assignment associated with transmission of a biological image, wherein
the first ratio is calculated based on at least one image capture condition of a plurality of image capture conditions,
the at least one image capture condition includes an image capture mode of the biological image,
the first ratio is of the bit assignment to a plurality of signal components of color information of irradiation light, and
the biological image is captured based on the irradiation light;
calculate a second ratio, associated with the bit assignment, based on a plurality of output characteristics of an output apparatus, wherein the output apparatus:
receives the biological image, and
outputs the received biological image;

change the bit assignment based on the first ratio and the second ratio;
increase a value of the bit assignment for a specific signal component of the plurality of signal components of the irradiation light based on the change in the bit assignment; and
control the transmission of the biological image based on the increase in the value of the bit assignment for the specific signal component of the irradiation light.

* * * * *